US00PP18478P2

(12) United States Plant Patent
Oudshoorn

(10) Patent No.: US PP18,478 P2
(45) Date of Patent: Feb. 12, 2008

(54) ***ASTRANTIA* PLANT NAMED 'FLORENCE'**

(50) Latin Name: *Astrantia major*
Varietal Denomination: Florence

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 90 days.

(21) Appl. No.: 11/520,926

(22) Filed: Sep. 14, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP12,697 P2 * 6/2002 Geerlings ..... Plt./263

OTHER PUBLICATIONS

Anonymous. "*Astrania* Hybride Florence". Available at: http://www.bakker–holland.hu/Catalog/Productdetail.aspx?parentcategoryname=33&selectedcatergoryname=40&productid=6031&R=6031–018.*

* cited by examiner

*Primary Examiner*—Wendy Haas
(74) *Attorney, Agent, or Firm*—C. A. Whealy

(57) ABSTRACT

A new and distinct cultivar of *Astrantia* plant named 'Florence', characterized by its upright plant habit; green-colored stems and leaves; freely and continuous flowering habit; and inflorescences with showy involucral bracts that are dark pink in color.

2 Drawing Sheets

Botanical designation: *Astrantia major.*
Cultivar denomination: 'Florence'.

BACKGROUND OF THE INVENTION

The present invention relates to a new and distinct cultivar of *Astrantia,* botanically known as *Astrantia major* and hereinafter referred to by the name 'Florence'.

The new *Astrantia* originated from an open-pollination in 2001 of an unnamed selection of *Astrantia major,* not patented, as the female, or seed, parent with an unknown selection of *Astrantia major,* as the male, or pollen, parent. The new *Astrantia* was discovered and selected by the Inventor as a single flowering plant from within the progeny of the stated open-pollination grown in a controlled environment in Rijpwetering Wetering, The Netherlands in 2003.

Asexual reproduction of the new cultivar by divisions in Rijpwetering, The Netherlands, since 2003, has shown that the unique features of this new *Astrantia* are stable and reproduced true to type in successive generations.

SUMMARY OF THE INVENTION

Plants of the cultivar Florence have not been observed under all possible environmental conditions. The phenotype may vary somewhat with variations in environment such as temperature and light intensity without, however, any variance in genotype.

The following traits have been repeatedly observed and are determined to be the unique characteristics of 'Florence'. These characteristics in combination distinguish 'Florence' as a new and distinct cultivar of *Astrantia:*

1. Upright plant habit.
2. Green-colored stems and leaves.
3. Freely and continuous flowering habit.

4. Inflorescences with showy involucral bracts that are dark pink in color.

Plants of the new *Astrantia* differ from plants of the female parent selection primarily in plant size and flower color.

Plants of the new *Astrantia* can be compared to plants of the *Astrantia* cultivar Snow Star, disclosed in U.S. Plant Pat. No. 12,697. In side-by-side comparisons conducted by the Inventor in Rijpwetering, The Netherlands, plants of the new *Astrantia* differed from plants of the cultivar Snow Star primarily in flower color as plants of the cultivar Snow Star had white-colored involucral bracts.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Astrantia.*

The photograph on the first sheet is a side perspective view of typical plants of 'Florence' grown in an outdoor nursery.

The photograph at the top of the second sheet is a close-up view of typical inflorescences of 'Florence'.

The photograph at the bottom of the second sheet is a close-up view of a typical leaf of 'Florence'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the late spring/early summer in an outdoor nursery in Rijpwetering, The Netherlands for about two years. During the production of the plants, day temperatures ranged from 14° C. to 27° C. and night temperatures ranged from 6° C. to 14° C.

Botanical classification: *Astrantia major* cultivar Florence.

Parentage:

*Female parent.*—Unnamed selection of *Astrantia major,* not patented.

*Male parent.*—Unknown selection of *Astrantia major,* not patented.

Propagation:

*Type.*—By divisions.

*Root description.*—Fine, fibrous; coppery brown in color.

*Rooting habit.*—Freely branching; dense.

Plant description:

*Form.*—Upright perennial flowering plant with basal rosette of leaves; numerous erect peduncles support umbels of flowers held well above the foliage. Moderately vigorous growth habit.

*Plant height.*—About 88 cm.

*Plant width.*—About 56 cm.

*Branch description.*—Arrangement: Branching mostly basal; freely branching, about 19 basal branches develop per plant. Length: About 69 cm. Diameter: About 5 mm. Internode length: About 21.3 cm. Strength: Strong. Aspect: Upright. Texture: Smooth, glabrous. Color: 144A.

Foliage description:

*Arrangement.*—Alternate, simple.

*Length, basal leaves.*—About 16.5 cm.

*Length, stem leaves.*—About 11.6 cm.

*Width, basal leaves.*—About 18.5 cm.

*Width, stem leaves.*—About 12.5 cm.

*Shape.*—Palmately-lobed.

*Apex.*—Acute.

*Base.*—Hastate.

*Margin.*—Doubly serrate.

*Texture, upper and lower surfaces.*—Smooth, glabrous.

*Venation pattern.*—Pinnate.

*Color.*—Developing foliage, upper surface: 143A. Developing foliage, lower surface: 143A to 143B. Fully expanded foliage, upper surface: 137B; venation, 143A to 137B. Fully expanded foliage, lower surface: 146B; venation, 143B.

*Petiole length, basal leaves.*—About 33.1 cm.

*Petiole length, stem leaves.*—About 5.1 cm.

*Petiole diameter, basal leaves.*—About 4.25 mm.

*Petiole diameter, stem leaves.*—About 6.5 mm.

*Petiole color, upper and lower surfaces.*—144A.

Inflorescence description:

*Inflorescence/flower arrangement and appearance.*—Numerous, single, minute campanulate flowers subtended by showy involucral bracts; flowers arranged in compound umbels. Flowers face mostly upright to somewhat outwardly. Very freely flowering; during the flowering season, typically about 80 flowers per umbel and about eight umbels per flowering stem develop.

*Natural flowering season.*—Continuous flowering from late spring to early summer in The Netherlands.

*Flower longevity on the plant.*—About twelve days; flowers not persistent.

*Fragrance.*—None detected.

*Flower buds.*—Length: About 1.5 mm. Diameter: About 1.5 mm. Shape: Oblate. Color: 138A; towards the apex, 75C to 75D.

*Inflorescence height.*—About 3.5 cm.

*Inflorescence diameter.*—About 4.9 cm.

*Flowers.*—Diameter: About 2 mm. Depth (height): About 9 mm.

*Petals.*—Arrangement: Five in a single whorl. Length: About 2.5 mm. Width: About 0.6 mm. Shape: Ovate. Apex: Narrowly acute. Margin: Entire. Texture, upper and lower surfaces: Smooth, glabrous. Color: When opening, upper and lower surfaces: 186C to 186D. Fully opened, upper and lower surfaces: 186C to 186D.

*Sepals.*—Arrangement: Five in a single whorl. Length: About 2 mm. Width: About 0.6 mm. Shape: Ovate. Apex: Broadly acute. Base: Cuneate. Margin: Entire. Texture, upper and lower surfaces: Smooth, glabrous. Color: When opening, upper and lower surfaces: 137C. Fully opened, upper and lower surfaces: 137C.

*Involucral bracts.*—Arrangement: About 20 in a single whorl. Length: About 2.4 cm. Width: About 7 mm. Shape: Elliptic to narrowly obovate. Apex: Acute. Base: Attenuate. Margin: Entire to slightly serrate. Texture, upper and lower surfaces: Smooth, glabrous. Color: When opening, upper and lower surfaces: 75C, towards the base, close to 75D; towards the apex, 137A to 137B. Fully opened, upper and lower surfaces: 65C to 65D; towards the apex, 137A; venation, 143A.

*Peduncles.*—Length: About 15.5 cm. Diameter: About 2 mm. Strength: Strong. Texture: Smooth, glabrous. Color: 144A.

*Pedicels.*—Length: About 5 mm. Diameter: About 0.3 mm. Strength: Strong. Texture: Smooth, glabrous. Color: 186D.

*Reproductive organs.*—Stamens: Quantity per flower: Five. Filament length: About 3.5 mm. Filament color: Lighter than 186D. Anther shape: Elliptical. Anther length: About 1 mm. Anther color: N167A to N167B. Pollen amount: Scarce. Pollen color: 161C to 161D. Pistils: Quantity per flower: Two. Pistil length: About 3 mm. Stigma shape: Club-shaped. Stigma color: 186C. Style length: About 2.8 mm. Style color: 186C. Ovary color: 143A; ribs, 142D.

*Seed/fruit.*—Seed and fruit production has not been observed.

Disease/pest resistance: Plants of the new *Astrantia* have not been noted to be resistant to pathogens and pests common to *Astrantia.*

Garden performance: Plants of the new *Astrantia* have exhibited good tolerance to rain, wind, high temperatures of 30° C. and are hardy to USDA Zone 6.

It is claimed:

1. A new and distinct *Astrantia* plant named 'Florence' as illustrated and described.

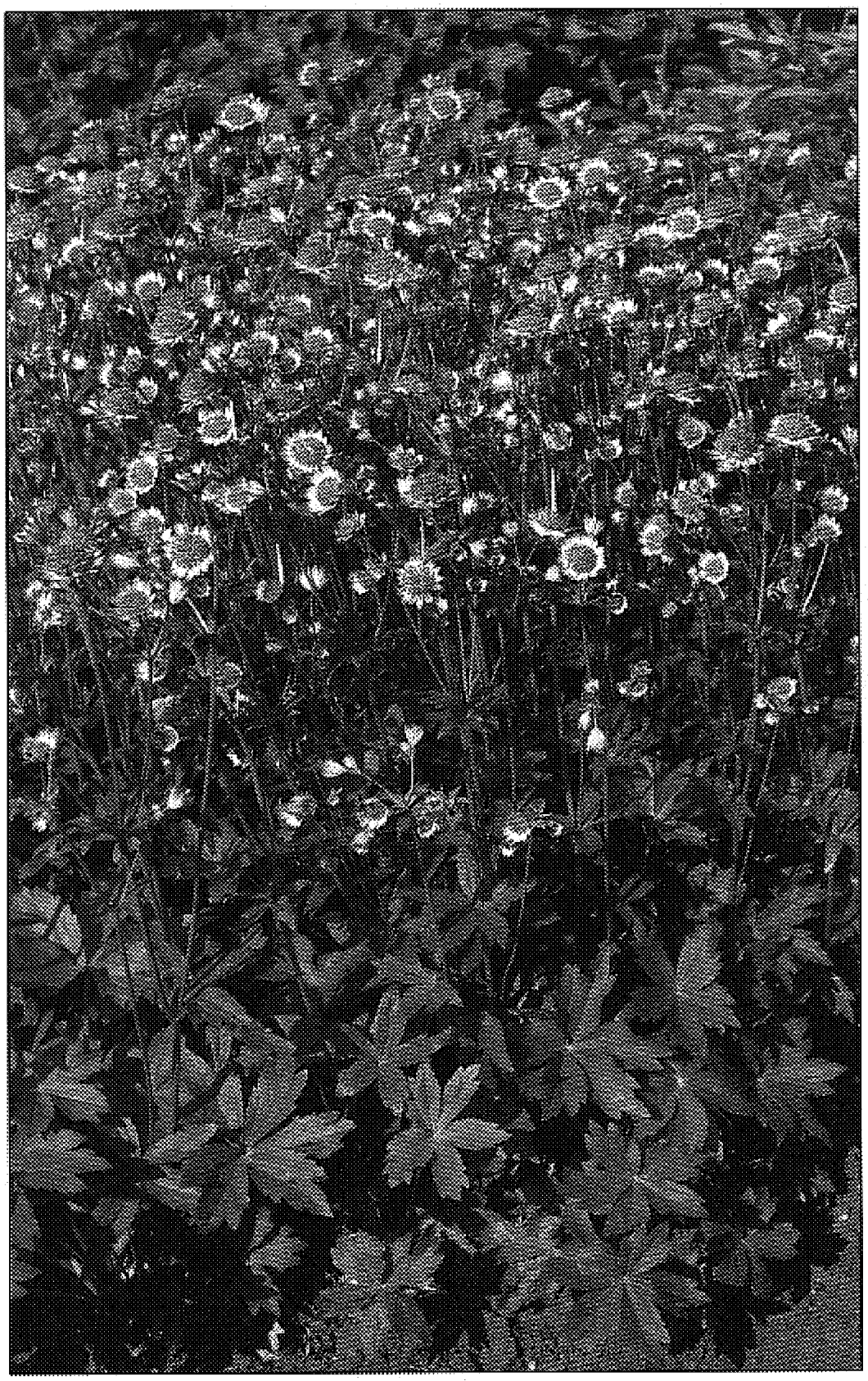

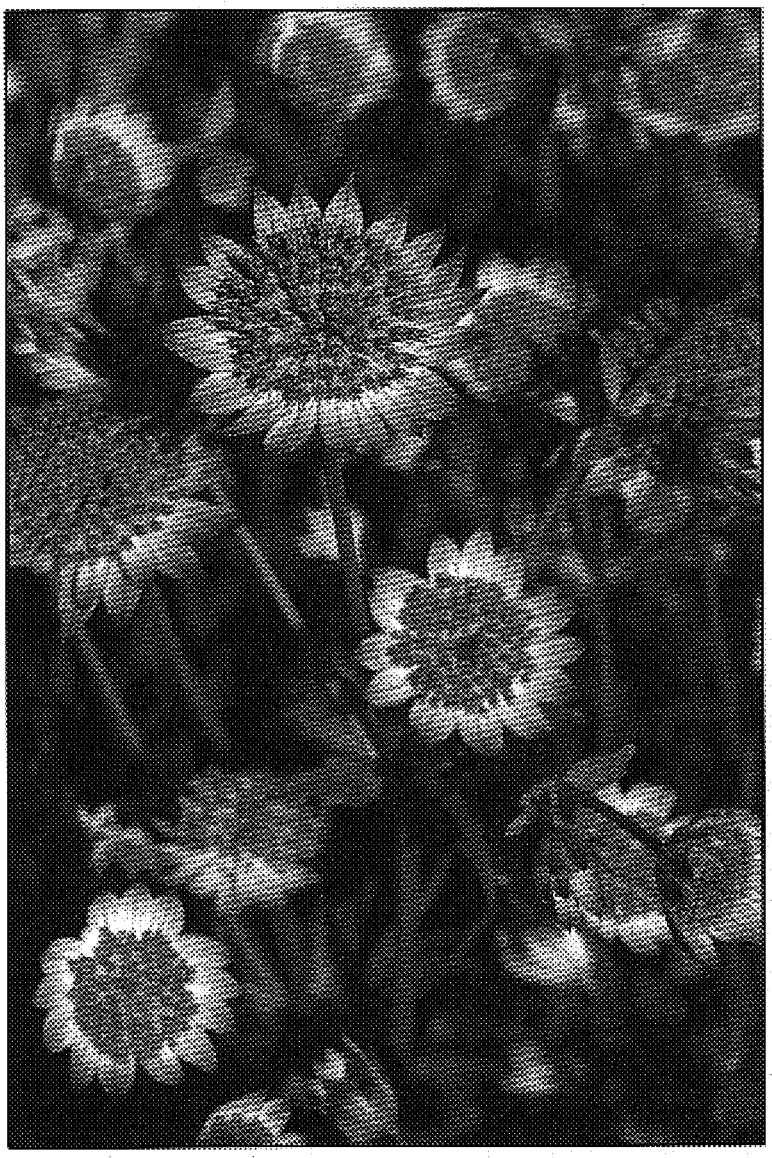
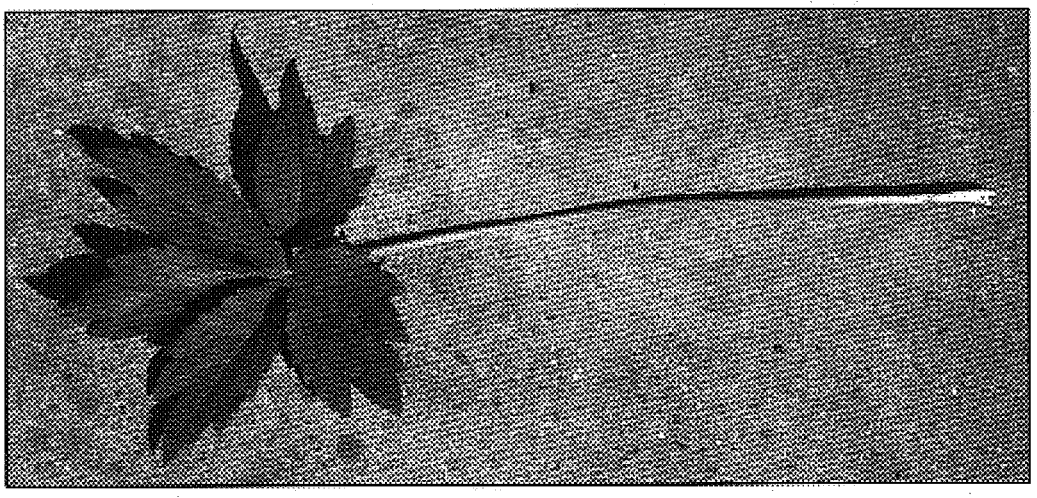

* * * * *